US00PP11264P

United States Patent [19]

Kordes

[11] Patent Number: Plant 11,264

[45] Date of Patent: Mar. 7, 2000

[54] MINIATURE ROSE PLANT NAMED 'KORMISSO'

[75] Inventor: Wilhelm Kordes, Sparrieshoop, Germany

[73] Assignee: Bear Creek Gardens, Inc., Medford, Oreg.

[21] Appl. No.: 09/073,021

[22] Filed: May 4, 1998

[51] Int. Cl.[7] ..... A01H 5/00

[52] U.S. Cl. ..... Plt./121

[58] Field of Search ..... Plt./121, 128, 122, Plt./129

[56] References Cited

U.S. PATENT DOCUMENTS

P.P. 6,875 6/1989 Marciel ..... Plt./121

*Primary Examiner*—Howard J. Locker

*Attorney, Agent, or Firm*—Klarquist Sparkman Campbell Leigh & Whinston

[57] ABSTRACT

Miniature rose plant having an ease to root from softwood cuttings; compact well-branched plant habit; rapid growth and free flowering; long flower life; long shelf life; and stable flower color.

1 Drawing Sheet

The present invention relates to a new and distinct variety of rose plant of the miniature class which was originated by me by discovering in a greenhouse in Sparrieshoop, Germany in the summer of 1995, a flower color mutation of the variety 'KORialie' (unpatented).

'KORmisso' is a dark pink flower color mutation of 'KORialie' (not patented) the flowers of which are a lighter pink. Like 'KORialie', it is an ideal pot rose, easy to root, grows rapidly, has a good pot rose habit, long shelf life, and stable flower color.

Asexual reproduction of this new variety by cutting propagation, as performed at Sparrieshoop, Germany, and Somis, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage: Spontaneous mutation of 'KORialie'.

Classification:

*Botanical.*—Rosa hybrida.

*Commercial.*—Miniature rose.

FLOWER

Observations made from specimens grown in a greenhouse environment at Sparrieshoop, Germany and at Somis, Calif. from January, 1997 to Febryary, 1998.

Blooming habit: Continuous.

Bud:

*Size.*—Three-fourths inch when the petals start to unfurl.

*Form.*—The bud form is long, pointed ovoid.

*Color.*—When sepals first divide, bud color is Red Group 54A. When half blown, the upper sides of the petals are Red Group 54B and the lower sides of the petals are Red Group 54B.

*Sepals.*—Color: Green Group 137B. Surface texture: Covered in fine hairs. There are three normally to heavily appendaged sepals. There are two unappendaged sepals with hairy edges.

*Receptacle.*—Color: Green Group 137D. Shape: Funnel. Size: Small (¼"×3⁄16"). Surface: Smooth.

*Peduncle.*—Length: Short (1½"). Surface: Glandular. Color: Green Group 137D. Strength: Stiff, erect.

Bloom:

*Size.*—Small. Average open size is 1¾ inches.

*Borne.*—Singly and in pyramidal clusters of three to five blooms.

*Stems.*—Short. Average length is five to five and one-half inches.

*Form.*—When first open: High centered. Permanence: Flattens, all petals curl quill fashion.

*Petalage.*—Number of petals under normal conditions: 50–60.

*Color.*—The upper sides of the petals are Red Group 54B. The reverse sides of the petals are Red Group 54B. The base of each petal has a distinctive (¼"×¼"), White Group 155D, half moon at the base of each petal. The major color on the upper sides is Red Group 54B.

*Variegations.*—Occasional greenish-white streak on guard petals and some on the petaloids.

*Discoloration.*—At the end of the first day: No change. At the end of the third day: No change. No change in flower color through day twelve or thirteen. At day thirteen or fourteen, there is a fading to Red Group 54C. Petal drop is day sixteen to day eighteen.

*Fragrance.*—None.

Petals:

*Texture.*—Leathery.

*Shape.*—Round to deltoid.

*Form.*—Tips slightly recurved, edges slightly quilled to moderately quilled.

*Arrangement.*—Imbricated. Petaloids in the center are many and small.

*Persistence.*—Petals drop off cleanly before drying.

*Lastingness.*—On the plant: Very long (sixteen to eighteen days). As a cut flower: Very long (twenty-one days).

Reproductive parts:

*Anthers.*—Size: Medium. Quantity: Many. Color: Yellow. Arrangement: Regular around styles mixed with petaloids.

*Filaments.*—Color: Yellow.
*Pollen.*—Color: Gold yellow.
*Styles.*—Color: Greenish-white.
*Stigmas.*—Color: Greenish-White.

Plant:
*Form.*—Bush.
*Growth.*—Vigorous; upright; branching; compact. In a garden environment, at maturity, height is sixteen to eighteen inches tall, width is fourteen to sixteen inches. When grown as a pot rose in a 10 cm pot, at maturity the plant is seven to eight inches in height and seven to eight inches wide.

Foliage: Number of leaflets on normal mid-stem leaves: Five.
*Size.*—Small (3 to 3¼" long×2 to 2½" wide).
*Quantity.*—Abundant.
*Color.*—New foliage: Upper and lower surfaces: Greyed-Orange Group 176B. Old foliage: Upper surface: Green Group 137A. Lower surface: Green Group 139C.
*Shape.*—Pointed oval.
*Texture.*—Upper side: Leathery, glossy.
*Edge.*—Serrated.
*Serration.*—Single, small.
*Petiole rachis.*—Color: Greyed-Purple Group 183C.
*Petiole underside.*—Rough with prickles and glands.
*Stipules.*—Short (⅜"), serrated.
*Disease resistance.*—Resistant to mildew under normal growing conditions at Sparrieshoop, Germany and Somis, Calif.

Wood:
*New wood.*—Color: Greyed-Orange Group 176B. Bark: Smooth.
*Old wood.*—Color: Green Group 137C. Bark: Smooth.

Prickles:
*Quantity.*—On main canes from base: Ordinary. On laterals from main canes: Ordinary.
*Form.*—Short, hooked downward.
*Color when young.*—Greyed-Purple Group 184C.

Small prickles:
*Quantity.*—On main stalks: None. On laterals: None.

I claim:

1. A new and distinct variety of miniature rose plant as herein shown and described characterized particularly by its ease of rooting from softwood cuttings; compact well-branched plant habit; rapid growth and free flowering; long flower life; long shelf life; and stable flower color.

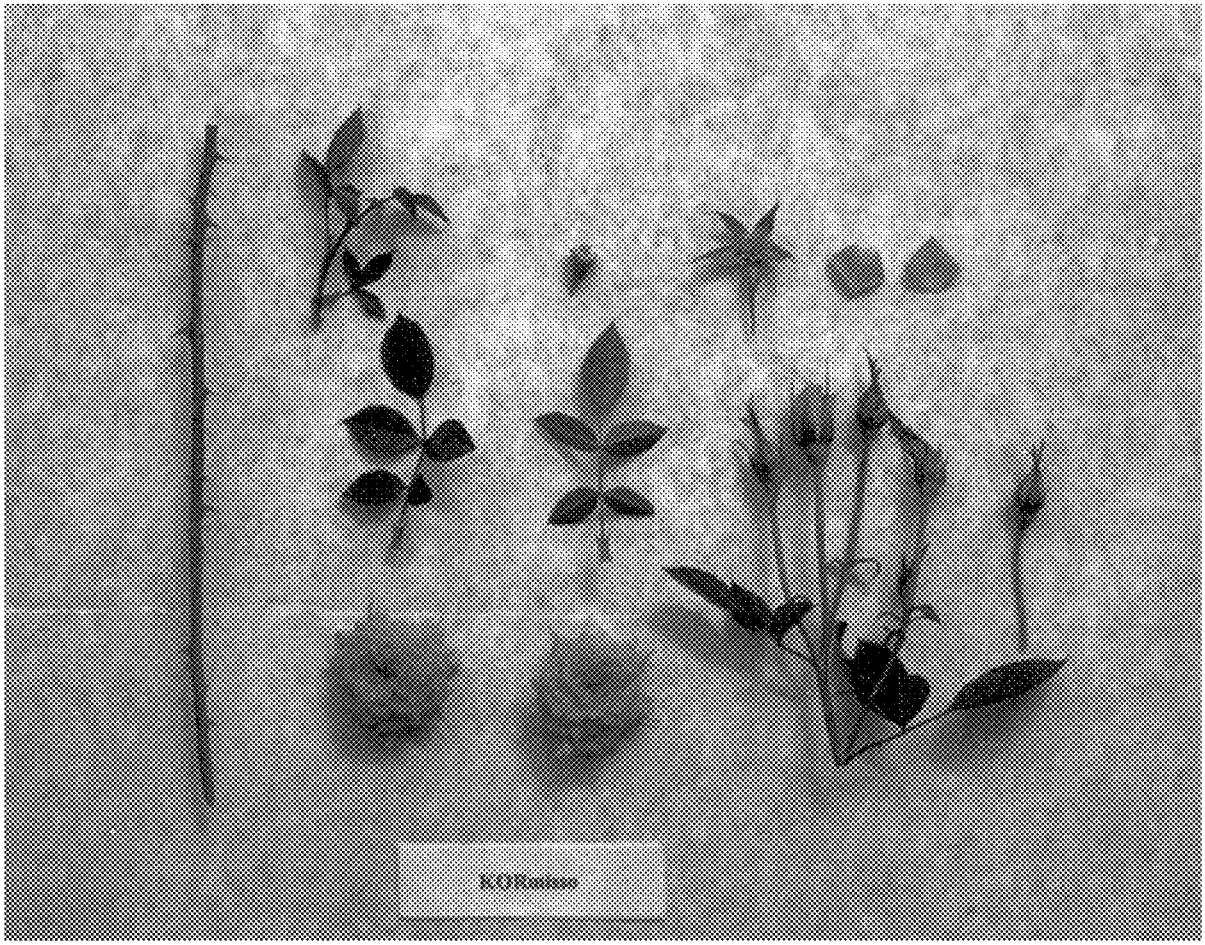

* * * * *